(12) United States Patent
Walta (10) Patent No.: US 6,260,560 B1
(45) Date of Patent: Jul. 17, 2001

(54) DEVICE AND METHOD FOR CLEANING AND/OR DISINFECTING ENDOSCOPES

(76) Inventor: Johannes Antonius Walta, Meidoornlaan 5, 2267 BA, Leidschendam (NL)

( * ) Notice: Subject to any disclaimer, the term of this patent is extended or adjusted under 35 U.S.C. 154(b) by 0 days.

(21) Appl. No.: 09/078,287

(22) Filed: May 13, 1998

(30) Foreign Application Priority Data

May 14, 1997 (NL) ................................................... 1006053

(51) Int. Cl.[7] ............................... A61L 2/00; B08B 9/032
(52) U.S. Cl. ................................. 134/22.12; 134/166 R; 134/169 R; 134/169 C; 422/28; 422/33; 422/292
(58) Field of Search ................................. 422/1, 28, 33, 422/292, 297, 293, 300; 134/166 R, 169 R, 169 C, 22.1, 22.11, 22.12, 22.18, 22.13, 22.14, 22.16, 22.17, 22.19; 604/264

(56) References Cited

U.S. PATENT DOCUMENTS 4,526,622 * 7/1985 Takamura et al. ..................... 422/33
5,225,160 * 7/1993 Sanford et al. ...................... 422/292
5,871,692 * 2/1999 Haire et al. ............................ 422/28

* cited by examiner

Primary Examiner—Jill Warden
(74) Attorney, Agent, or Firm—Helfgott & Karas, P.C.

(57) ABSTRACT

For the purpose of cleaning and/or disinfecting endoscopes having a plurality of channels, each channel is connected to a feedline, which is provided with a shut-off valve, for a cleaning and/or disinfecting agent, and each channel is flushed with a cleaning and/or disinfecting agent. If necessary, before flushing the channels, separating means are arranged in the endoscope in order to separate channels from one another, in such a manner that during flushing only single channels are present in the endoscope. Each single channel is connected to a feedline for a cleaning and/or disinfecting agent and is flushed separately. The single channels which merge in the endoscope into a common channel part are flushed one after the other. Advantageously, if single channels of mutually different passage width are flushed simultaneously, an additional flow restriction is arranged in at least the feedline connected to the channel with the greater passage width.

14 Claims, 7 Drawing Sheets

DEVICE AND METHOD FOR CLEANING AND/OR DISINFECTING ENDOSCOPES

BACKGROUND OF THE INVENTION

The invention relates to a device and a method for cleaning and/or disinfecting endoscopes having a plurality of channels.

A known device for cleaning and/or disinfecting endoscopes with a plurality of channels is disclosed in European patent application EP 0 709 056. This known device comprises at least one rinsing basin, in which an endoscope which is to be cleaned and/or disinfected can be placed, a housing in which, inter alia, a system of lines, pumps and valves is accommodated for the purpose of feeding a cleaning and/or disinfecting agent to an endoscope which has been placed in a rinsing basin, means for connecting the channels of an endoscope which has been placed in the rinsing basin to the system of lines, pumps and valves, and control means for controlling the pumps and valves, the system of lines, pumps and valves comprising a feedline for a cleaning and/or disinfecting agent for each endoscope channel, each feedline having an outlet which can be connected to the endoscope channel and a shut-off valve which is accommodated in the feedline.

The shut-off valves of the feedlines are accommodated in a unit which is connected on one side to the system of lines, pumps and valves and on the other side is provided with outlets to which the endoscope channels can be connected. When this device is used for cleaning and/or disinfecting an endoscope with a plurality of channels each channel is connected to a feedline for a cleaning and/or disinfecting agent and flushed with a cleaning and/or disinfecting agent. When flushing the endoscope channels with a cleaning and/or disinfecting agent channels of substantially the same passage width are flushed simultaneously.

In other known cleaning and disinfection systems for endoscopes, all the channels are flushed simultaneously.

The known cleaning and disinfection systems for endoscopes have the drawback that the cleaning and disinfection is not always optimal. This drawback is related to the design of the most usual types of endoscopes. Various types of endoscopes have two or more channels, the diameter of which varies between 0.8 and 4.2 mm. A standard type of endoscope has two channels with a relatively large passage width, the suction channel and the biopsy channel, of a diameter which lies between 2.0 and 4.5 mm, three channels with a relatively small passage width, the air channel, the water channel and the jet channel, of a diameter of, for example, 0.7 mm, and a very narrow channel, the so-called lift channel. The lift channel has to be considered as a channel with an internal diameter of 0.5 mm, in which a screw thread with an external diameter of 0.3 mm is accommodated, so that a gap of 0.1 mm remains. Moreover, endoscopes have a complex system of channels in which, for reasons of compactness, two channels frequently merge into a common channel part which has a double function. This merging takes place in the head part of the endoscope. Thus, for example, the air channel and the water channel are combined to form an air/water channel, and the suction and the biopsy channel are combined to form a suction/biopsy channel. In certain types of endoscopes, three channels may even merge to form a common channel part. A drawback of this merging of channels into a common channel part is that when the channels are flushed simultaneously during the cleaning and/or disinfection the flow in one of the channels may decrease or even come to a standstill. As a result, there is a risk that the channel in question will be insufficiently cleaned and/or disinfected, or will not be cleaned and/or disinfected at all.

SUMMARY OF THE INVENTION

The object of the invention is to overcome the drawback of the known cleaning and disinfection systems and to provide a system which ensures optimum cleaning and disinfection of all the channels present in the endoscope.

This object is achieved according to the invention by means of a device for cleaning and/or disinfecting endoscopes having a plurality of channels, comprising at least one rinsing basin, in which an endoscope which is to be cleaned and/or disinfected can be placed, a housing in which, inter alia, a system of lines, pumps and valves is accommodated for the purpose of feeding a cleaning and/or disinfecting agent to an endoscope which has been placed in a rinsing basin, means for connecting the channels of an endoscope which has been placed in the rinsing basin to the system of lines, pumps and valves, and control means for controlling the pumps and valves, the system of lines, pumps and valves comprising a feedline for a cleaning and/or disinfecting agent for each endoscope channel, each feedline having an outlet which can be connected to the endoscope channel and a shut-off valve which is accommodated in the feedline, and the control means being designed such that different types of endoscopes can be cleaned and/or desinfected and that during cleaning and/or disinfecting of an endoscope each channel of the endoscope is flushed separately with a cleaning and/or disinfecting agent and channels which merge into a specific common channel part are flushed one after the other.

This object is also achieved by a method for cleaning and/or disinfecting an endoscope having a plurality of channels comprising the steps of arranging, if necessary, separating means in the endoscope in order to separate channels from each other so that during cleaning and/or disinfecting of the endoscope only single channels are present in the endoscope, connecting each single channel to a feedline for a cleaning and/or disinfecting agent, and flushing each single channel with a cleaning and/or disinfecting agent, single channels which merge in the endoscope into a specific common channel part being flushed one after the other.

The device and method according to the invention allow all the separate channels in the endoscope to be flushed, so that the cleaning and disinfection system is more efficient and operationally reliable than the known systems. The system according to the invention furthermore has the additional advantage that the cleaning and disinfection process can be carried out at room temperature, so that the adverse effects of cleaning and disinfecting at elevated temperature (for example 60° C.) are eliminated.

DETAILED DESCRIPTION OF A PREFERRED EMBODIMENT

Figure 1:
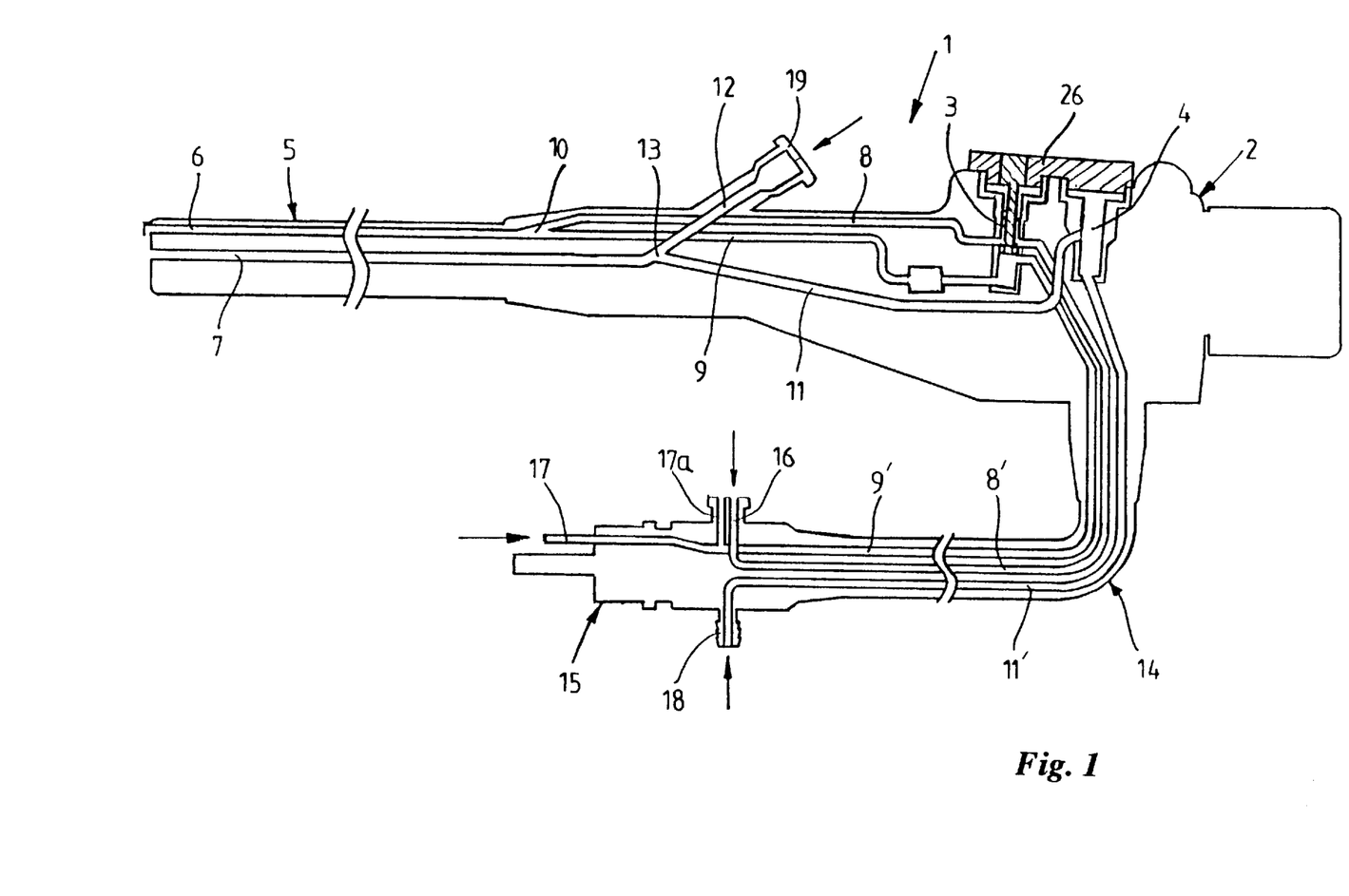
FIG. 1 diagrammatically shows a certain type of endoscope.

FIG. 1 shows an endoscope 1 with a head part 2, in which openings 3 and 4 are formed, in which, during normal use of the endoscope, an air/water valve and a suction valve are arranged. A flexible insertion hose 5 is attached to the head part 2, in which hose a combined air/water channel 6 and a combined suction/biopsy channel 7 are accommodated.

A separate air channel 8 and water channel 9, which at the location of a joining point 10 merge into the air/water channel 6, are arranged in the head part 2. Furthermore, a separate suction channel 11 and biopsy channel 12, which at the location of the joining point 13 merge into the suction/biopsy channel 7, are accommodated in the head part 2.

In the head part 2, the air channel 8 and the water channel 9 open into the opening 3 for the air/water valve. The suction channel 11 opens into the opening 4 for the suction valve. Furthermore, a flexible feed hose 14 is connected to the head part 2, in which hose there are accommodated channels 8', 9' and 11' which, via the openings 3 and 4, are connected to the air channel 8, the water channel 9 and the suction channel 11, respectively. In practice, the feed hose 14 is also referred to as the light-conductor casing.

The mutually connecting channels 8 and 8', 9 and 9', 11 and 11' will be referred to below overall as the air channel 8, the water channel 9 and the suction channel 11.

A connection 16 for the air channel 8, connections 17 and 17a for the water channel 9 and a connection 18 for the suction channel 11 are arranged on the end section 15 (also referred to as the light conductor connector) of the flexible hose 14. When connection 16 is in use, connection 17a is closed off. A connection 19 for the biopsy channel 12 is arranged on the head part 2.

Figure 2:
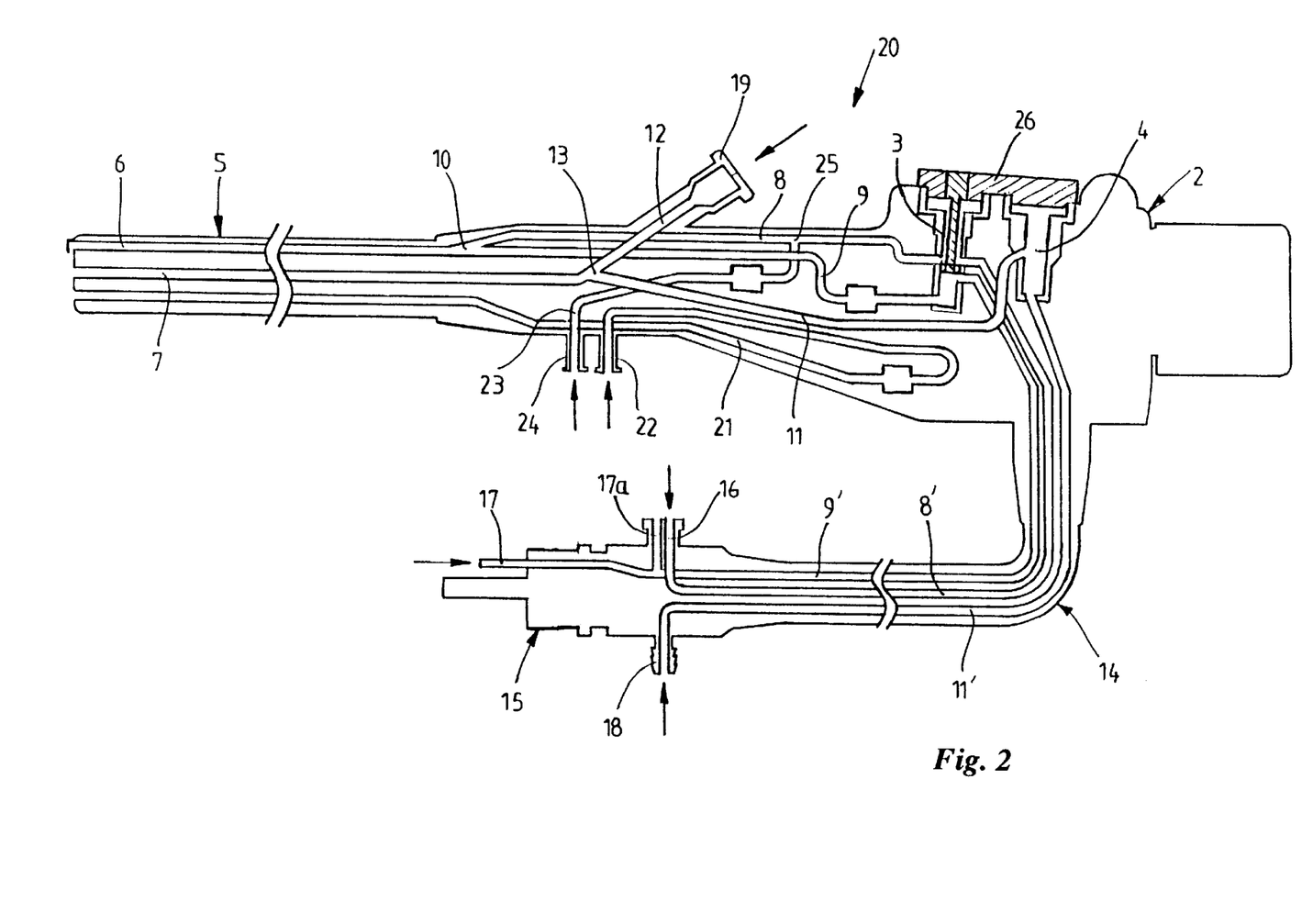
FIG. 2 diagrammatically shows another type of endoscope.

FIG. 2 shows an endoscope 20 which differs from the endoscope illustrated in FIG. 1 by the fact that it is provided with an additional channel 21 with connection 22 and an additional channel 23 with the connection 24. In the head part 2, the channel 23 is connected to the air channel 8 at the joining point 25.

In the endoscopes illustrated in FIGS. 1 and 2, for the purpose of cleaning and/or disinfecting, an auxiliary separating piece 26 is arranged in the openings 3 and 4 instead of the air/water valve and the suction valve, in such a manner that the air channel 8 and the water channel 9 are channels which are continuous but separate from one another and the suction channel 11 is a continuous channel. In this way, there are only single channels present in the endoscope during the cleaning and disinfection process, or at least the channels are separated from one another in such a manner that they can be flushed separately.

Figure 3:
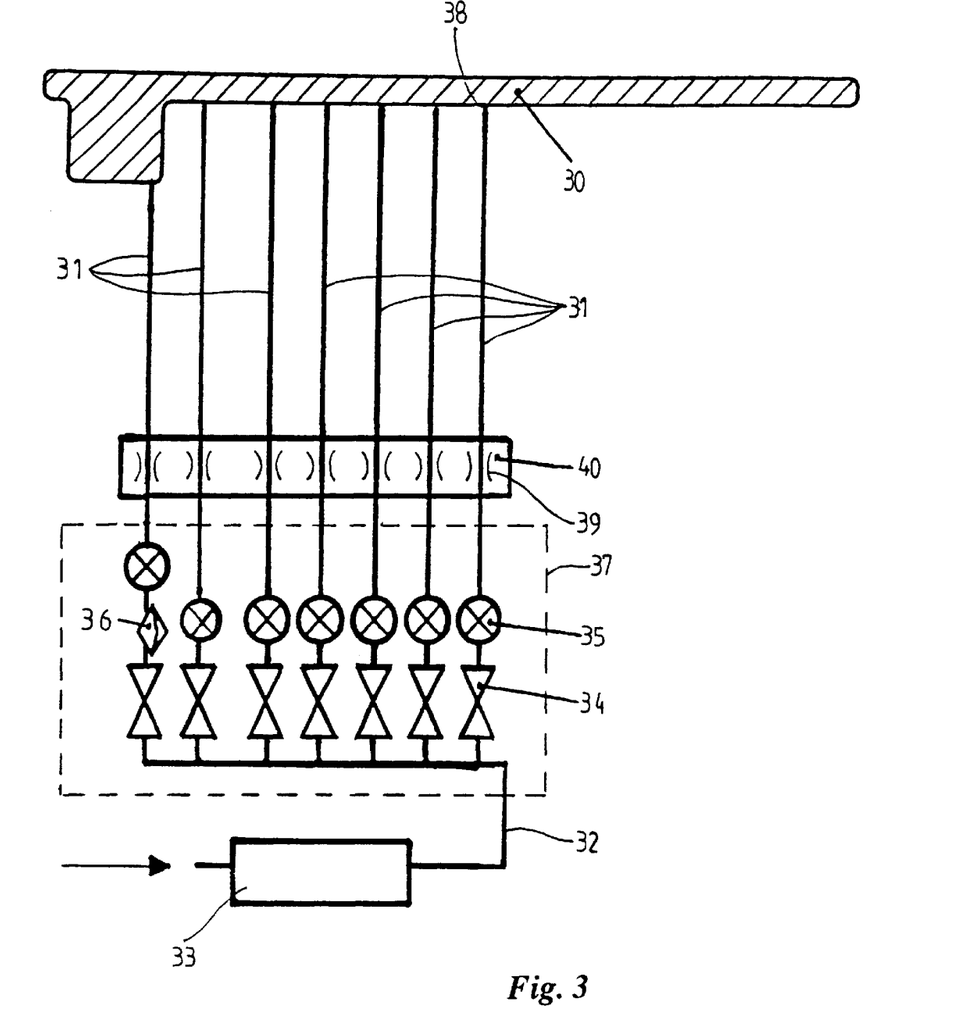
FIG. 3 very diagrammatically shows the connection of an endoscope to the connection section of a device for cleaning and/or disinfecting according to the invention.

FIG. 3 diagrammatically depicts the connection of an endoscope 30 which is to be cleaned and/or disinfected to a device for cleaning and disinfecting endoscopes. The various channels in the endoscope 30, as described with reference to FIGS. 1 and 2, are connected to feedlines 31 for cleaning and/or disinfecting agent. The feedlines 31 are connected to a common line 32, in which a feed pump 33 is incorporated. A shut-off valve 34 and a pressure sensor 35 is incorporated in each feedline 31. An additional pump (lifting pump) 36 is accommodated in one of the feedlines 31, the feedline to the lift channel in the endoscope. The shut-off valve 34, the pressure sensors 35 and the lifting pump 36 may be accommodated in a separate unit 37.

Such an unit 37 may be part of a known device known for cleaning and disinfecting endoscopes which is described extensively in European patent application EP 0 709 056, which document should be regarded as part of the present description.

In the device according to the invention, as can be seen in FIG. 3, an extra flow restriction 39 is incorporated in each feedline 31 between the shut-off valve 34 and the connection 38 to an endoscope channel. In FIG. 3, the various restrictions 39 are accommodated in a connection block 40 which is positioned between the unit 37 and the connections 38.

When flushing the channels in the endoscope, the restrictions have a balancing effect on the pressure and the flow of the cleaning or disinfecting agent. Using the restrictions makes it possible to simultaneously flush an endoscope channel having a wide passage width and an endoscope channel having a narrow passage width, without one of the channels being insufficiently flushed through, which would result in insufficient cleaning and/or disinfection of the channel in question. The flow resistance of the flow restrictions is usually in the order of magnitude the flow resistance of the endoscope channel having the narrow passage width.

In the method according to the invention, after the above-mentioned separating means (auxiliary separating piece 26) have been arranged in the endoscope and the single channels in the endoscope have been connected to the feedlines 31 for cleaning and/or disinfecting agent, the single channels in the endoscope are flushed separately.

Figure 4:
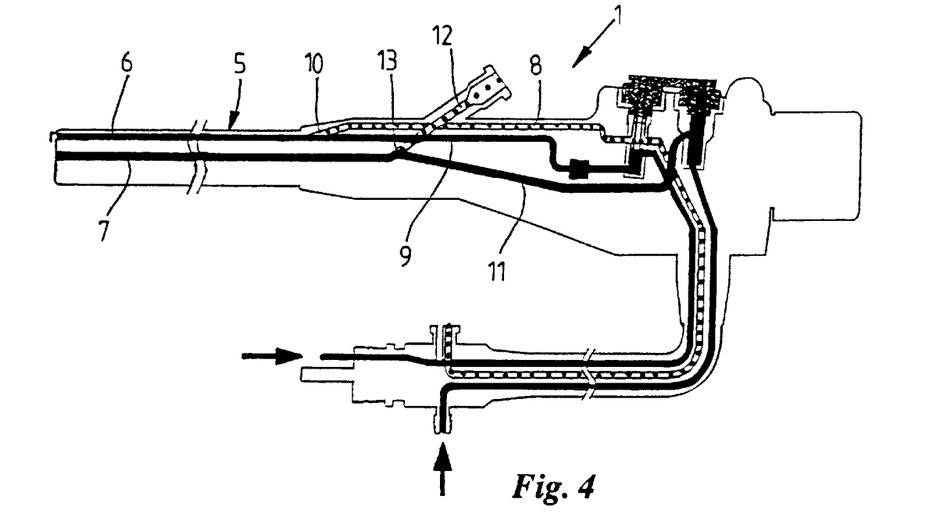
FIGS. 4 and 5 show the phases of flushing the channels in an endoscope of the type shown in FIG. 1 during the cleaning and/or disinfecting.
Figure 5:
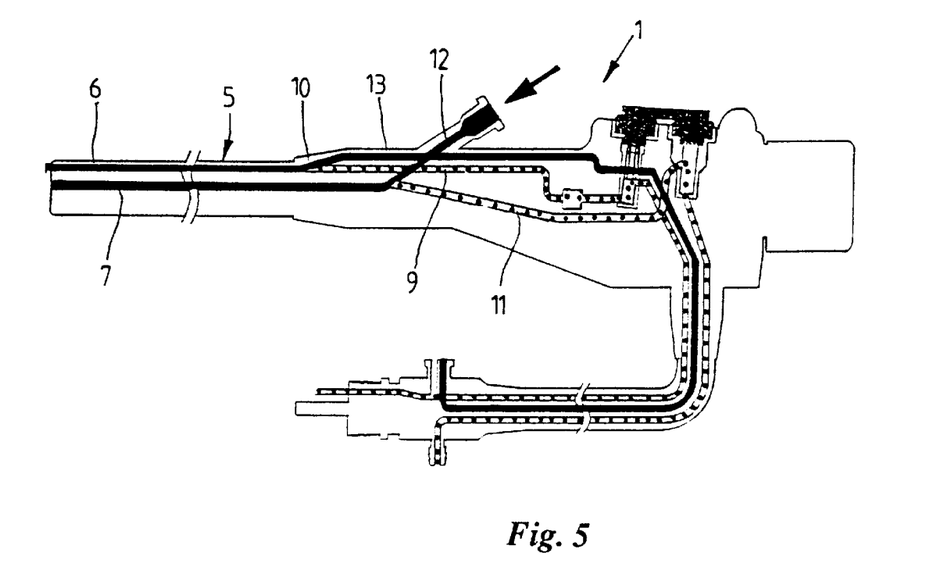

In an endoscope 1 of the type shown in FIG. 1, the channels are flushed through in two phases, which are depicted in FIGS. 4 and 5.

In the first phase (FIG. 4), the water channel 9 and the suction channel 11 are flushed. The shut-off valves 34 in the feedlines 31 to the water channel 9 and the suction channel 11 are then opened. The shut-off valves 34 in the feedlines 31 to the air channel 8 and the biopsy channel 12 are closed. As a result, the rinsing liquid cannot flow back via the joining point 10 and the air channel 8 and via the joining point 13 and the biopsy channel 12, respectively.

Owing to the restrictions 39 in the feedlines 31, it is possible in this phase to simultaneously flush a channel having a small passage width (water channel 9) and a channel having a large passage width (suction channel 11), while ensuring that both channels are flushed adequately.

In the second phase (FIG. 5), the air channel 8 and the biopsy channel 12 are flushed. The shut-off valves 34 in the feedlines which were opened in the first phase are now closed, and vice versa.

The channels 6 and 7 in the insertion hose 5 are flushed in both phases.

Obviously, it is also possible to flush the biopsy channel 12 in the first phase and the suction channel 11 in the second phase.

Figure 6:
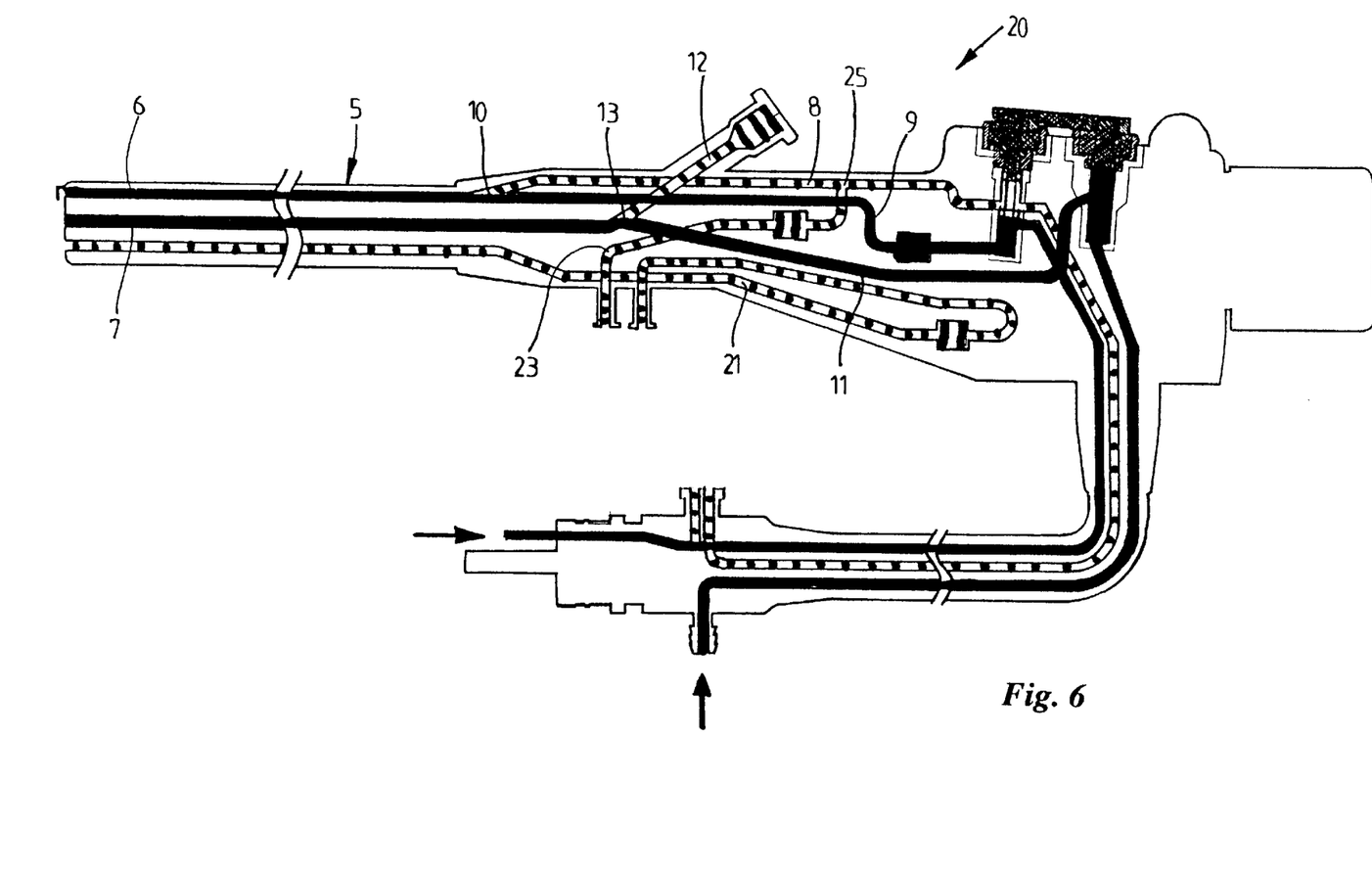
FIGS. 6 to 8 show the phases of flushing the channels in an endoscope of the type shown in FIG. 2 during the cleaning and/or disinfecting.
Figure 7:
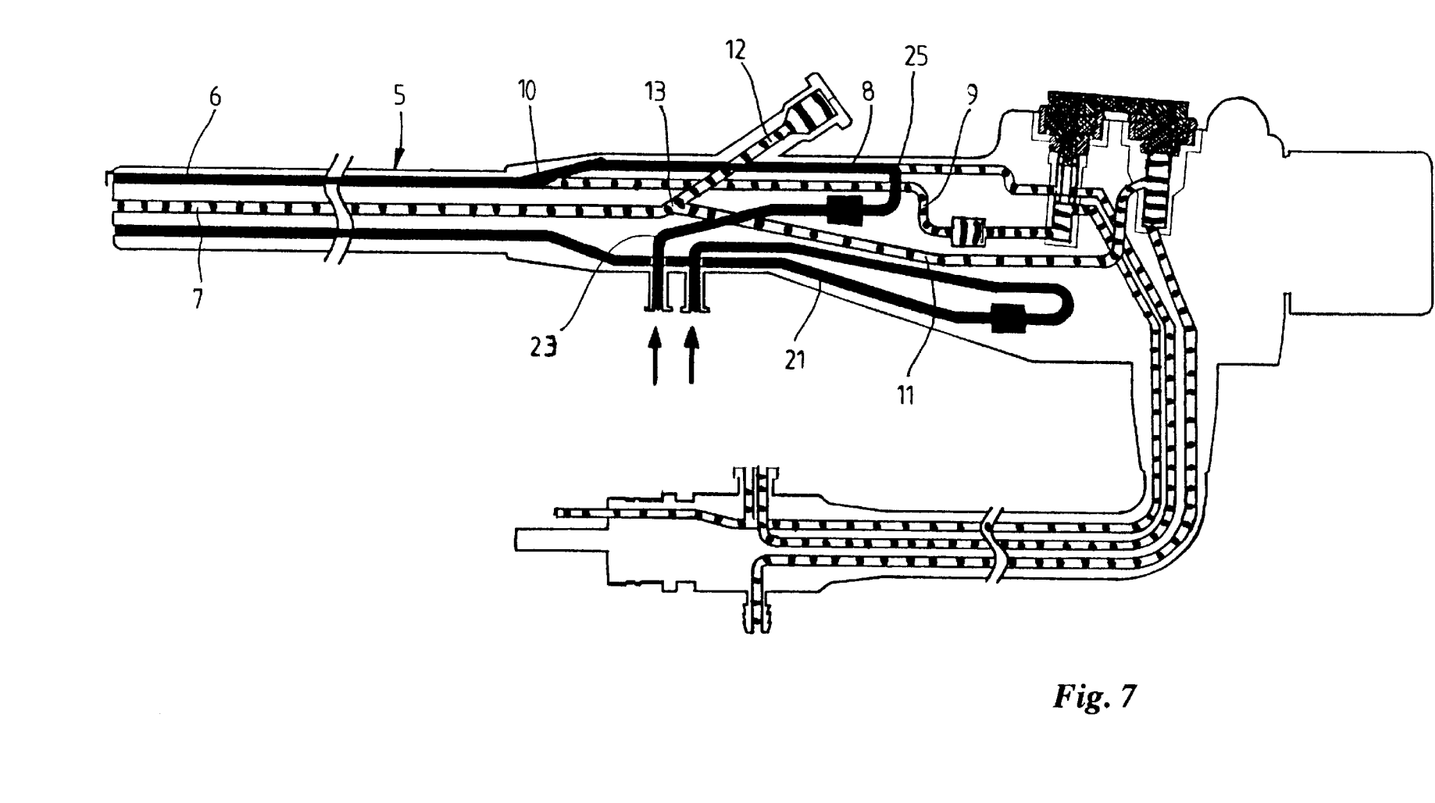
Figure 8:
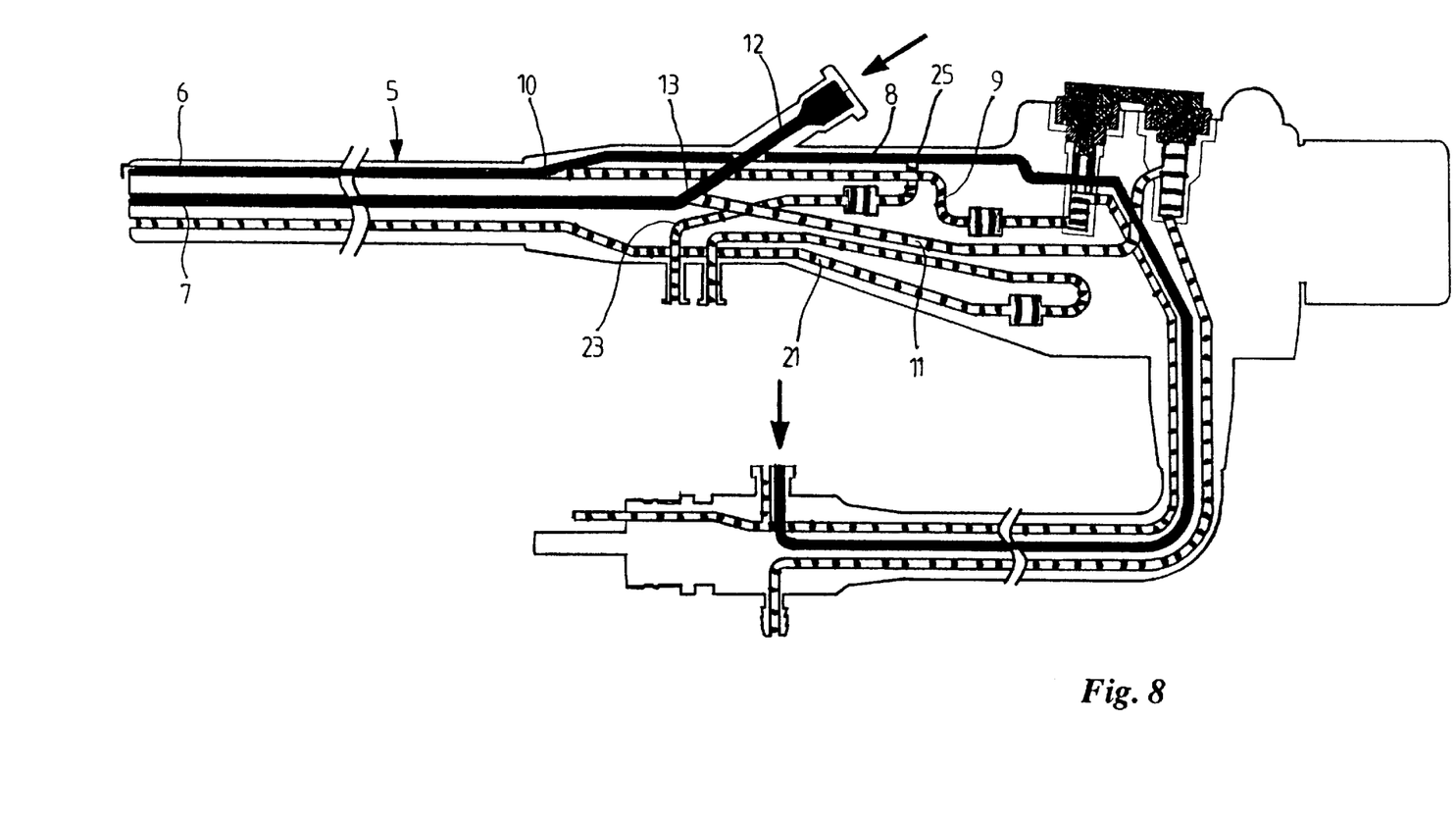

In an endoscope 20 of the type illustrated in FIG. 2, the flushing takes place in three phases, which are illustrated in FIGS. 6 to 8.

The first and third phases (FIGS. 6 and 8) substantially correspond to the first and second phases of FIGS. 4 and 5, provided that in both the first and the third phase the shut-off valves 34 in the feedlines to the channels 21 and 23 are also closed.

In the second phase (FIG. 7), the shut-off valves 34 in the feedlines 31 to the lines 21 and 23 are opened and the shut-off valves 34 in the feedlines 31 to the air channel 8, the water channel 9, the suction channel 11 and the biopsy channel 12 are closed.

It should be noted that the channel 21 could also be flushed in the first or third phase, since this channel has no connection with the other channels.

It will be clear that channels may also be flushed simultaneously in a different combination in the various phases, as long as channels which open out into a common channel part are not flushed simultaneously.

What is claimed is:

1. A device for flushing internal channels of an endoscope having a plurality of channels, comprising:

a feeding system for feeding a fluid flushing agent to an endoscope;

means for connecting said channels of said endoscope to the feeding system;

control means for controlling the feeding system, said feeding system including:

a respective feedline for said flushing agent for each endoscope channel to be flushed, each feedline having an outlet for connection to an endoscope channel and a shutoff valve which is upstream of said outlet, the control means being programmable such that different types of endoscopes can be flushed, in use of said device during flushing of an endoscope each channel of said endoscope being flushed with said flushing agent separately under programmed direction of said control system, said control system being programmed to flush one after the other any channels which merge into a common channel part in said connected endoscope.

2. The device of claim 1, wherein the control means are programmable such that during flushing of one of the channels merging into a common channel part, the feedline/feedlines to the other channel/channels merging into the common channel part is/are closed off.

3. The device of claim 1, wherein at least one feedline has an additional flow restriction.

4. The device of claim 3, further comprising an unit in which the shut-off valves of the feedlines are accommodated, and a connection block wherein the flow restrictions are accommodated, said connection block being connected directly to the unit containing the shut-off valves.

5. The device of claim 1, further comprising at least one rinsing basin in which an endoscope which is to be flushed can be placed, and a housing for said device.

6. The device of claim 3, wherein said additional restriction is between the shut-off valve and the outlet.

7. The method of claim 1, wherein during flushing of one of the single channels merging into a specific common channel part the feedline/feedlines to the other single channels opening into the common channel part is/are closed off.

8. The method of claim 1, wherein when single channels of mutually different passage widths are flushed simultaneously, comprising a further step of providing an additional flow restriction in at least the feedline connected to the channel in said endoscope with the greater passage width.

9. The method of claim 8, wherein the flow resistance of the flow restrictions is of the same order of magnitude as that of the channel having the narrowest passage width.

10. A method for flushing an endoscope having a plurality of channels comprising the steps of:

positioning separating means in the endoscope to separate channels from each other so that during flushing of the endoscope only single channels are present in the endoscope;

connecting each single channel to a feedline for a flushing agent, and flushing each single channel with said flushing agent, single channels which merge in the endoscope into a common channel part being flushed one after the other.

11. The method of claim 10, wherein during flushing of one of the single channels merging into a specific common channel part, the feedline/feedlines to the other single channels opening into the common channel part is/are closed off.

12. The method of claim 10, wherein when single channels of mutually different passage widths are flushed simultaneously, comprising a further step of providing an additional flow restriction in at least the feedline connected to the channel in said endoscope with the greater passage width.

13. The method of claim 12, wherein flow resistance of the flow restrictions is of the same order of magnitude as that of the channel having the narrowest passage width.

14. A method for flushing an endoscope having a plurality of channels comprising the steps of:

connecting each single channel to a feedline for a flushing agent, and flushing each single channel with said flushing agent, single channels which merge in the endoscope into a common channel part being flushed one after the other.

* * * * *